United States Patent [19]

Ahmed et al.

[11] Patent Number: 5,663,286

[45] Date of Patent: Sep. 2, 1997

[54] NONWOVEN WEB COMPRISING WATER SOLUBLE POLYAMIDES AND ARTICLES CONSTRUCTED THEREFROM

[75] Inventors: Sharf U. Ahmed, Woodbury; Greg J. Van Lith, Mounds View, both of Minn.

[73] Assignee: H.B. Fuller Licensing and Financing, Inc., St. Paul, Minn.

[21] Appl. No.: 555,524

[22] Filed: Nov. 9, 1995

[51] Int. Cl.$^6$ .................... C08G 69/26; C08G 73/10
[52] U.S. Cl. .................... 528/339; 528/310; 528/335; 528/338; 528/339.3; 528/340; 528/347; 428/474.4; 604/358
[58] Field of Search .................... 528/335, 339, 528/338, 340, 347, 339.3, 310; 604/358; 428/474.5

[56] References Cited

U.S. PATENT DOCUMENTS

| | | | |
|---|---|---|---|
| 3,882,090 | 5/1975 | Fagerberg et al. | 528/339 |
| 5,086,162 | 2/1992 | Speranza et al. | 528/339 |
| 5,118,785 | 6/1992 | Speranza et al. | 528/325 |
| 5,254,668 | 10/1993 | Dominguez et al. | 528/323 |
| 5,324,812 | 6/1994 | Speranza et al. | 528/338 |
| 5,456,982 | 10/1995 | Yansen et al. | 428/370 |
| 5,486,419 | 1/1996 | Clementini et al. | 428/397 |

*Primary Examiner*—Samuel A. Acquah
*Assistant Examiner*—P. Hampton-Hightower
*Attorney, Agent, or Firm*—Carolyn A. Fischer; Nancy N. Quan

[57] ABSTRACT

This invention relates to a nonwoven web comprising a water soluble polyamide and articles constructed therefrom. The water soluble polyamide may be used alone or in combination with conventional thermoplastic web forming materials such as water insoluble polyethylene, polypropylene, polyester and polyamide. The water soluble polyamide may also be combined with biodegradable or selectively dispersible material to form nonwoven webs having various combinations of properties. Such water soluble webs have utility in the manufacture of disposable absorbent articles such as disposable diapers, feminine napkins, incontinent products and cellulosic articles such as tissues and towels, as well as for water soluble heat fusible webs for the textile industry.

20 Claims, No Drawings

NONWOVEN WEB COMPRISING WATER SOLUBLE POLYAMIDES AND ARTICLES CONSTRUCTED THEREFROM

FIELD OF THE INVENTION

This invention relates to a nonwoven web comprising a water soluble polyamide and articles constructed therefrom. The water soluble polyamide may be used alone or in combination with conventional thermoplastic web forming materials such as water insoluble polyethylene, polypropylene, polyester and polyamide. The water soluble polyamide may also be combined with biodegradable or selectively dispersible material to form nonwoven webs having various combinations of properties. Such water soluble webs have utility in the manufacture of disposable absorbent articles such as disposable diapers, feminine napkins, incontinent products and cellulosic articles such as tissues and towels, as well as for water soluble heat fusible webs for the textile industry.

BACKGROUND OF THE INVENTION

Melt blown and spunbond webs typically comprise insoluble and nondegradable polymers such as water insoluble polyethylene, polypropylene, polyester and polyamide. Such webs are used in the manufacture of a variety of disposable products such as disposable diapers, feminine napkins, surgical gowns, laundry bags, bed pads, and the like. Such articles are designed to absorb and contain bodily fluids and/or provide a physical barrier to such fluids. Water soluble and biodegradable nonwoven webs may provide some solutions to environmental concerns regarding the disposal of such items.

Heat fusible webs are used for a variety of uses. In the textile industry, heat fusible webs are used to hold pieces of fabric, such as a patch pocket, in place prior to being sewn. These heat fusible webs are also used to create hems on pants or for a variety of ornamental craft appliqués. Webs currently available for such uses are typically low viscosity at application temperature and insoluble in water. Upon activation with heat these materials often soak into the fabric workpiece causing the fabric to become stiff. Often the melted web soaks in to the extent that it fails to form the intended bond and reapplication is necessary.

A water soluble nonwoven comprising polyvinyl alcohol (PVOH) is taught in Dever et at., JP 59041260. Modifying the rate of water solubility of a PVOH based melt blown material using two different chemical treatments is described in the *Development and Evaluation of Water Soluble Melt Blown Nonwovens*, Dever, Benson, and Pair, INDA JNR, Vol. 5, No. 2, published 1993.

PVOH as a base polymer for the formation of a water soluble web suffers from several disadvantages. Due to its high melt point and poor thermal stability, it is very difficult to thermally process. An extruder, rather than merely a melt tank, is required to process the PVOH into a web. Additionally, once the web is formed, it has poor heat seal properties such that it would need to be heat sealed at temperatures that adversely affect the integrity of the substrate.

Water soluble polyamide prepared from adipic acid and polyoxyethylene diamine is reported by Fagerberg et al., U.S. Pat. No. 3,882,090 and Speranza et al., U.S. Pat. Nos. 5,086,162, 5,324,812 and 5,118,785. However, no such compositions have been used to form a water soluble nonwoven web or combined with other fibers to form nonwoven webs exhibiting a variety of properties.

The applicants have found that certain water soluble polyamides exhibit improved melting characteristics for manufacturing spunbond and melt blown nonwoven webs.

SUMMARY OF THE INVENTION

The present invention is a nonwoven web comprising a water soluble polyamide and articles constructed therefrom. The water soluble polyamide may be used alone or in combination with conventional thermoplastic web forming materials such as water insoluble polyethylene, polypropylene, polyester and polyamide. The water soluble polyamide may also be combined with biodegradable or selectively dispersible material to form nonwoven webs having various combinations of properties. The nonwoven web may be formed from spunbond and melt blown techniques as well as be sprayed molten or in an aqueous dispersion form.

Furthermore, the polyamide may be sprayed or dispersed in water to be used as a binder bonding fibers in air laid or wet laid processes. This aspect is particularly useful for improving the strength of cellulosic absorbent products such as tissues and towels. The resulting nonwoven can be used to form laminates such as those found in disposable articles to incorporate hydrophilic and water soluble features into the product. Such water sensitivity may facilitate recycling and composting efforts related to solid waste management as well as improve fluid transfer and acquisition. Additionally, nonwoven webs comprising a water soluble polyamide are useful for making water soluble heat fusible webs. A 4,7,10 trioxatridecane-1,13-diamine is preferred due to its low melt temperature. Since the resulting web will dissolve during washing, such a web will overcome the problems of insoluble heat fusible webs used for temporary bonding in the textile industry.

DETAILED DESCRIPTION OF THE INVENTION

The present invention is a nonwoven web comprising a water soluble polyamide. Such polyamides are taught by the above identified Fagerberg and Speranza patents and are produced by reacting at least one polyalkylene glycol diamine with at least one dicarboxylic acid or esters thereof.

The polyalkylene glycol diamine has the formula:

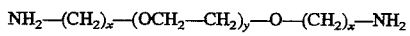

$$NH_2-(CH_2)_x-(OCH_2-CH_2)_y-O-(CH_2)_x-NH_2$$

wherein X ranges from 2 to 3 and Y ranges from 1 to 2. Representative examples include triethylene glycol diamine, wherein X=2 and Y=1, and tetraethylene glycol diamine, wherein X=2 and Y=2. Commercial diamines of such include Jeffamine®148 amine and Jeffamine®192 amine. The preferred diamine is 4,7,10- trioxatridecane-1,13-diamine (TTD diamine) wherein X=3 and Y=2.

Suitable dicarboxylic acids are those having from 5 to 36 carbon atoms including adipic acid, pimelic acid, azelaic acid, sebacic acid, dodecanedioic acid, terephthalic acid, isophthalic acid, t-butyl isophthalic acid, dimer acid and mixtures thereof. The esters and anhydrides of these acids may also be used. Adipic acid is preferred.

The resulting water soluble polyether amide preferably has a melt point about 190° C. or less as the case when adipic acid is reacted with Jeffamine®148. More preferably, the melt point is about 155° C. or less as the case when adipic acid is reacted with Jeffamine®192. The most preferred water soluble polyether amide has a melt point about 150° C. or less as the case when adipic acid is reacted with TTD dime. This particular combination results in a faster setting, strong, easily processed water soluble polyether amide. The low melt temperature makes this combination particularly preferred for heat fusible webs. Often heat fusing such webs at temperatures above 150° C. adversely affects the integrity of the substrates to be bonded. The resulting web is insoluble in dry cleaning solvent rendering the article (fabric) dry cleanable when necessary.

The resulting polyamide may be formed into a web by means of known melt blown or spunbond techniques. Alternatively, the polyamide may be sprayed molten or as an aqueous dispersion during other nonwoven manufacturing processes such as air laid or wet laid processes to bind fibers and impart strength.

The polyamide may be used alone or in combination with other polymers to create a variety of useful properties in the resulting web. By combining the water soluble polyamide with conventional insoluble polymers such as polyethylene, polypropylene, polyester or polyamide sequentially during the web forming process, the resulting web will have a water soluble matrix. Preferably, the insoluble polymer is applied to form a discontinuous web. The water soluble polyamide is then applied to the discontinuous regions such that the resulting web dissolves at the locations of the polyamide leaving small portions of the insoluble portions intact. Alternatively, the water soluble polyamide may be applied as a continuous phase with discontinuous regions of the insoluble polymer. This technique creates a low cost flushable web. By combining the water soluble polyamide with at least one insoluble polymer simultaneously, it is possible to create webs having hydrophilic character that do not disperse in water.

The polyamide may additionally be combined with biodegradable materials or selectively dispersible materials to create nonwoven webs having unique combinations of properties. As in the case of the more conventional polymers, depending on the method, sequences and ratios by which they were combined, the web may or may not be water dispersible. If the polyamide is added sequentially during the web forming process, each material tends to maintain its unblended properties, whereas simultaneously combining the polyamide in the melt phase with at least one other polymer results in webs with properties intermediate between the unblended polymers. The polymer present at the higher concentration tends to govern the overall properties of the nonwoven web.

Useful biodegradable polymers include those which as photodegradable, microbiologically and hydrolytically degradable, as well as cellulosics so long as the polymer can be incorporated into a web either alone or combined with a compatible carrier. Representative Examples include polylactic acid, polyhydroxybutyrate, polyhydroxybutyratevalerate, polycaprolactone, and mixtures thereof.

Selectively dispersible polymers include those which are dispersible in aqueous environment under prescribed conditions, yet are not dispersible in all aqueous environments. Examples include materials that are alkaline dispersible or saline insoluble. The Eastman AQ copolyesters, which are water dispersible yet saline insoluble are preferred for articles intended to absorb body fluids.

EXAMPLES

Example 1

A water soluble polyamide was produced by reacting adipic acid with TTD diamine such that the resulting polyamide had a viscosity of about 10,000 cps to about 12,000 cps at 400° F. as measured by a Brookfield viscometer. Preferably, stearic acid is utilized at concentrations of about 0.5–2% to control the viscosity. Reaction conditions are maintained at a temperature of about 400° F. or as low as possible to insure the resulting polyamide is light in color. The polyamide was sprayed with a Bayer and Otto hotmelt spray gun to form a nonwoven web. The polyamide was premelted at 400° F. in an oven and sprayed onto release paper while maintaining an application temperature ranging from about 390° F. to 400° F. At a pressure of about 40 psi, the basis weight of the web was 72.5 g/m$^2$ whereas at a pressure of 60 psi the basis weight was reduced to 33.9 g/m$^2$. The applicants surmise that nonwoven web may be formed with commercial meltdown or spunbond web forming equipment at temperatures ranging from about 375° F. to 400° F. The polyamide was also used to form a nonwoven web with J & M meltblown hot melt spray applicators at a temperature of 400° F. Both webs were readily soluble in tap water such that a 1"×1" piece will solubilize in approximately 20 minutes without agitation.

Example 2

A second polyamide was produced from the same reactants as Example 1 without stearic acid such that the viscosity is about 35,000 cps at 400° F. The polyamide was sprayed with a Bayer and Otto hotmelt spray gun at a temperature of about 400° F. The basis weight can be adjusted with the air pressure as in Example 1. The resulting nonwoven web resembled conventional spunbond nonwoven formed from water insoluble polyester or polypropylene, yet the web is readily soluble in tap water.

Example 3

The polyamide of Example 2 was combined with a compatible water insoluble polyamide produced by reacting primarily dimer acid with ethylene diamine such that the viscosity of the water insoluble polyamide was about 58,000 cps at 400° F. The polyamides were melted and combined at a ratio of 4 parts water soluble polyamide to 1 part insoluble polyamide and at a ratio of 1 part water soluble polyamide to 4 parts water insoluble polyamide. The blended polyamides were then sprayed with a Bayer and Otto spray gun at a temperature ranging from about 410° F. to 420° F. to form a web resembling conventional meltblown or spunbond nonwoven. The web formed from 4 parts water soluble polyamide readily disperses in tap water. The web formed from 1 part water soluble polyamide is not dispersible in water, yet is hydrophilic. Therefore, blends of small concentrations of water soluble polymers with insoluble polymers are useful for imparting hydrophilicity into nonwoven webs. This is particularly useful for creating hydrophilic zones in line for disposable absorbent products.

Example 4

An Eastman AQ copolyester having an intrinsic viscosity of about 0.2 was sprayed on both sides of the water soluble web formed in Example 1. The Eastman AQ copolyesters are soluble in water, yet saline or body fluid insoluble. The resulting web disperses in water yet is not dispersible upon submersion in saline for 45 minutes.

Example 5

The water soluble polyamide of Example 1 was sprayed simultaneously with an experimental biodegradable polymer, Eastman Polyester 14766, to form a fused nonwoven web. Upon placing the web in water, some dissolution was observed yet the web remained intact due to the presence of the polyester. This combination is particularly preferred for disposable diapers as a possible solution for solid waste management concerns. When the water soluble polyamide was combined with the Eastman Polyester 14766 sequentially, the discreet webs could be easily separated from each other. Applicants surmise the polyamide could be sprayed simultaneously with any water insoluble polymer that is suitable for web forming processes.

Example 6

The water soluble webs of Examples 1 and 2 are heat fusible. Examples 3–5 may also be heat fusible, but will no longer be 100% soluble. In order to compare the properties of the improved water soluble web of the present invention, it was compared to PVOH. Although nonwoven web comprising PVOH are known, such webs are not commercially available. Applicants attempted to create a nonwoven web with hot melt spray applications as in Examples 1–5.

Vinex 2019, PVOH commercially available from Air Products was heated at 170° C. After 30 minutes the Vinex 2019 had turned light brown due to degradation. Since the material was unflowable at 170° C., the temperature was increased to about 210° C. upon which the Vinex 2019 turned very dark in appearance and fumed. Therefore, such attempts were unsuccessful due to the poor thermal stability and processability to PVOH.

Since a nonwoven web could not be formed from PVOH without the extrusion meltblown equipment taught by Dever, Benson and Pair in the INDA publication mentioned above, the applicants formed a film from an aqueous emulsion to compare the heat seal properties. A 15% aqueous solution of Vinex 2019 and a 15% aqueous solution of the water soluble polyamide of Example 1 were used to cast films. Upon drying, the thickness of the resulting fills was about 1 to 2 mils.

The films were cut into pieces and used to heat seal standard copy paper with a small iron. Table 1 depicts the results of the heat seal bonds and this demonstrates the improved properties of the water soluble polyamide with respect to PVOH.

TABLE 1

| Temperature | Time | Results |
| --- | --- | --- |
| 290–305° F. | 1 Minute | Vinex 2019 Did not bond the paper. It stuck to the side which was pressed by iron but peeled off easily when cooled. No fiber tear. |
| 290–305° F. | 1 Minute or 30 Seconds | Example 1 Gave excellent bond. Gave fiber tear. |
| 390–410° F. | 1 Minute | Vinex 2019 Only bonded to the paper side which was directly in contact with iron, but did not bond paper on both sides. |
| 390–410° F. | 30 Seconds | Example 1 gave excellent bonds and fiber tear. |

What is claimed is:

1. A nonwoven web comprising a water soluble polyether amide produced by reacting at least one polyalkylene glycol diamine with at least one dicarboxylic acid or ester thereof, said polyalkylene glycol diamine has the formula:

$$NH_2-(CH_2)_x-(OCH_2-CH_2)_y-O-(CH_2)_x-NH_2$$

wherein X ranges from 2 to 3 and Y ranges from 1 to 2; wherein said web is produced by spraying said water soluble polyether amide in molten form.

2. The nonwoven web of claim 1 wherein at least one of said polyalkylene glycol diamines is 4,7,10-trioxatridecane-1,13-diamine.

3. The nonwoven web of claim 1 wherein said water soluble polyether amide is produced by reacting 4,7,10-trioxatridecane-1,13-diamine with at least one dicarboxylic acid or esters thereof.

4. The nonwoven web of claim 1 further comprising at least one polymer selected from the group consisting of a biodegradable polymer, a water insoluble polymer, an alkaline dispersible polymer, a saline insoluble water dispersible polymer, and mixtures thereof.

5. The nonwoven web of claim 4 wherein said biodegradable polymer is selected from the group consisting of polylactic acid, polyhydroxybutyrate, polyhydroxybutyratevalerate, polycaprolactone, and mixtures thereof.

6. The nonwoven web of claim 4 wherein the water insoluble polymer is selected from the group consisting of polyethylene, polypropylene, polyester, polyamide and mixtures thereof.

7. The nonwoven web of claim 1 wherein said web is heat fusible at a temperature of less than about 155° C.

8. A disposable article comprising the nonwoven web of claim 1.

9. A disposable absorbent article comprising the nonwoven web of claim 4.

10. A disposable absorbent article comprising the nonwoven web of claim 6.

11. The article of claim 8 wherein said article is selected from the group consisting of disposable diapers, feminine napkins, surgical gowns, and bed pads.

12. The article of claim 9 wherein said article is selected form the group consisting of disposable diapers, feminine napkins, surgical gowns, and bed pads.

13. The article of claim 10 wherein said article is selected from the group consisting of disposable diapers, feminine napkins, surgical gowns, and bed pads.

14. A cellulosic absorbent having improved strength comprising a water soluble polyamide.

15. The article of claim 14 further comprising a biodegradable polymer.

16. The article of claim 14 further comprising an alkaline dispersible polymer, a saline insoluble water dispersible polymer and mixtures thereof.

17. A flushable, disposable article comprising a nonwoven web having portions of at least one water soluble polyamide and portions of a water insoluble polymer in contact with each other.

18. A flushable, disposable article of claim 17 wherein said water soluble polyamide portions form a continuous matrix.

19. A flushable, disposable article of claim 17 wherein said water soluble polyamide portions substantially surrounds said water-insoluble polymer portions.

20. The nonwoven web of claim 1 wherein said water soluble polyether amide is sprayed at a temperature of less than about 400° F.

* * * * *